United States Patent [19]

Randolph et al.

[11] Patent Number: 5,489,727
[45] Date of Patent: Feb. 6, 1996

[54] ISOPENTANE DISPROPORTIONATION

[75] Inventors: Bruce B. Randolph; Marvin M. Johnson, both of Bartlesville, Okla.

[73] Assignee: Phillips Petroleum Company, Bartlesville, Okla.

[21] Appl. No.: 450,448

[22] Filed: May 25, 1995

Related U.S. Application Data

[63] Continuation-in-part of Ser. No. 330,419, Oct. 28, 1994, abandoned.

[51] Int. Cl.$^6$ ..................................................... C07C 6/10
[52] U.S. Cl. ........................... 585/702; 585/706; 585/708; 585/709; 585/710; 585/723
[58] Field of Search ..................................... 585/702, 706, 585/708, 709, 710, 723

[56] References Cited

U.S. PATENT DOCUMENTS

| | | | |
|---|---|---|---|
| 2,403,649 | 7/1946 | Frey | 260/683.5 |
| 2,403,650 | 7/1946 | Frey | 260/683.5 |
| 2,405,993 | 8/1946 | Burk | 196/78 |
| 3,679,771 | 7/1972 | Hutson, Jr. et al. | 260/676 R |
| 3,686,354 | 8/1972 | Hervert | 260/683.43 |
| 5,382,744 | 1/1995 | Abbott et al. | 585/709 |

*Primary Examiner*—E. Rollins Cross
*Assistant Examiner*—Timothy H. Meeks
*Attorney, Agent, or Firm*—K. K. Brandes

[57] ABSTRACT

The disproportionation of isopentane(s) in the presence of hydrogen fluoride as the catalyst is improved by adding at least one $C_6$–$C_{18}$ (preferably $C_6$–$C_8$) isoalkane to the isopentane feed.

25 Claims, No Drawings

ISOPENTANE DISPROPORTIONATION

This application is a continuation-in-part of U.S. patent application Ser. No. 08/330,419, filed Oct. 28, 1994, now abandoned.

BACKGROUND OF THE INVENTION

The conversion of isopentanes to alkanes (paraffins) containing fewer carbon atoms per molecule and alkanes containing more carbon atoms per molecule (i.e., the disproportionation of isopentanes) in the presence of hydrogen fluoride as a catalyst is known and has been described in U.S. Pat. Nos. 2,403,649, 2,403,650 and 3,679,771. This process has recently gained importance because of governmental regulations requiring the reduction of the amount of volatile $C_4$ and $C_5$ alkanes in gasoline. Thus, there is an incentive to convert isopentanes to higher isoalkanes, especially isoheptanes and isooctanes which are valuable high-octane motor fuels, and to isobutane which is a feedstock for the alkylation with olefins and also for the production of MTBE (via isobutylene). The present invention is directed to an improvement of the HF-catalyzed disproportionation of isopentane.

SUMMARY OF THE INVENTION

It is an object of this invention to improve the disproportionation of isopentanes (2-methylbutane and/or 2,2-dimethylpropane) to isobutane and $C_6+$ alkanes. Other objects and advantages of the present invention will be apparent from the detailed description and the appended claims.

In accordance with this invention, in a process for disproportionating isopentanes in the presence of hydrogen fluoride as the catalyst at effective disproportionation conditions, the improvement comprises adding at least one higher isoalkane additive containing 6–18 (in particular 6–10) carbon atoms per molecule to a liquid feed comprising at least one isopentane so as to increase the conversion of said at least one isopentane to isobutane and to higher product alkanes which contain at least 6 carbon atoms per molecule. Preferably, the formed disproportionation product is then subjected to a separation process, wherein hydrogen fluoride, unconverted isopentane and at least one unconverted isoalkane additive are separated from the remainder of the disproportionation product (primarily isobutane and $C_6+$ product alkanes) and are then recycled to the disproportionation reaction zone.

DETAILED DESCRIPTION OF THE INVENTION

The feed for the process of this invention can be any hydrocarbon-containing feed which comprises at least one isopentane (2-methylbutane or 2,2-dimethylpropane or mixture thereof). Generally, the feed contains more than about 50 weight-% isopentane(s), preferably about 60–99.99 weight-% isopentane(s). The feed can contain other hydrocarbons which do not interfere with the process of this invention, such as minor amounts of other alkanes, e.g., n-butane, isobutane, n-pentane, n-hexane and the like. Alkenes (monoolefins) and other unsaturated compounds are to be substantially absent from the feed so as to avoid side reactions, such as alkylation.

Any effective amount of at least one higher isoalkane additive (i.e., one $C_6$–$C_{18}$ or two or more than two $C_6$–$C_{18}$ isoalkanes) can be employed in the process of this invention. Generally, the weight ratio of added higher isoalkane additive to isopentane in the feed is in the range of about 0.02:1 to about 1:1, preferably about 0.05:1 to about 1:1, more preferably about 0.1:1 to about 1:1, most preferably about 0.3:1 to about 0.7:1. Preferred higher isoalkane additives contain 6–16 (more preferably 6–8) carbon atoms per molecule, and include (but are not limited to) 2,3-dimethylbutane, 2,2-dimethylbutane, 2-methylhexane, 3-methylhexane, 4-methylhexane, 2,3-dimethylpentane, 3,3-dimethylpentane, 2,4-dimethylpentane, 3-ethylpentane, 2-methylheptane, 3-methylheptane, 4,-methylheptane, 2,2-dimethylhexane, 2,3-dimethylhexane, 2,4-dimethylhexane, 2,5-dimethylhexane, 3-ethylhexane, 2,2,3-dimethylpentane, 2,2,4-trimethylpentane, 2,3,3-trimethylpentane, 2,3,4-trimethylpentane, 2-methyl-3-ethylpentane, isononanes, isodecanes, isoundecanes, isododecanes, isotridecanes, isotetradecanes, isopentadecanes, isohexadecanes, and mixtures of two or more of the above isoalkanes. Presently preferred additives are 2,3-dimethylbutane, 2,3-dimethylpentane and 2,2,4-trimethylpentane, and isoalkanes containing 12–16 carbon atoms per molecule.

Any effective reaction conditions can be employed in he disproportionation process of this invention. Generally the reaction temperature is about 100°–250° F. (38°–121° C.), preferably about 180°–210° F. (82°–99° F.). Generally the reaction pressure is about 200–400 psig (14–28 atm. gauge). Generally, the volume ratio of liquid anhydrous hydrogen fluoride (HF) catalyst to liquid hydrocarbon feed is about 0.1:1 to about 4:1, preferably about 1:1 to about 3:1, more preferably about 1.5:1 to about 2.5:1. The reaction can be carried out as a batch process in an autoclave (generally with agitation) or as a continuous process. In the latter case, the feed rate of the liquid hydrocarbon feed can vary widely depending on the dimensions of the reactor (generally a reactor tube made of a corrosion-resistant metal, optionally equipped with static mixing means), the desired feed throughput and the desired isopentane conversion.

The disproportionation product comprises a variety of substances: HF, unconverted isopentane(s), isobutane, small amounts of n-butane and propane, n-hexane, isohexanes, n-heptane, heptanes, octanes, nonanes, decanes and higher alkanes, including unconverted $C_6$–$C_{18}$ isoalkane additive(s). The various product components are separated from each other by any suitable separation means (preferably fractional distillation), either at an elevated pressure or at atmospheric conditions (after depressurization of the product). Generally, the product is separated into the following main fractions: HF, isobutane, unconverted isopentane(s), isohexanes, and $C_7+$ isoalkanes (mainly isoheptanes, isooctanes, isononanes). Separated HF, unconverted isopentanes and isohexanes are generally recycled to the disproportionation reactor. Detailed separation and recycling procedures depend on the specific isoalkane additive and can be determined by those skilled in the art.

The following example is presented to further illustrate this invention and is not to be construed as unduly limiting the scope of the invention.

EXAMPLE

A Monel autoclave reactor (volume: 300 ml), which was equipped with a mechanical stirrer, a thermocouple, a pressure gauge and various valves, was filled with about 150 grams (about 161 ml) of anhydrous hydrogen fluoride (HF). The reactor content was slowly stirred, and its temperature was raised from room temperature to about 190° F. (about 88° C.). Thereafter, the stir rate was increased to about 1500 rpm, and 75 mL isopentane was charged to the reactor via a feed sight gauge by means of pressurized nitrogen gas.

After a reaction time of about 30 minutes, at a $N_2$ pressure of about 250 psig (i.e., about 17.2 atm. gauge) and a reaction temperature ranging from about 182° F. (about 83° C.) to about 202° F. (about 94° C.), the stirring of the reactor was stopped, and the product was withdrawn from the reactor. First, the product was allowed to settle in a sight gauge settler for about 30 seconds, and then it was passed through a column of alumina beads (¼ inch diameter) so as to remove soluble HF from the product. The product was analyzed by means of a gas chromatograph.

In the two control runs, 75 mL of a liquid feed containing about 99 weight-% isopentane (the remainder being mainly n-pentane and n-hexane) was employed. In the invention runs, a higher isoalkane was also present in the feed (total volume: about 75 mL), at a volume ratio of the added higher isoalkane to isopentane ranging from about 1:20 to about 1:2. The volume ratio of anhydrous HF to the entire hydrocarbon feed (isopentane alone in control runs; a mixture of isopentane and a higher isoalkane in the invention runs) was about 2:1 in all tests. Pertinent test results are summarized in Table I.

That which is claimed:

1. In a process for disproportionating isopentanes in the presence of a catalyst so as to form alkanes containing fewer than five carbon atoms per molecule and alkanes containing more than five carbon atoms per molecule, the improvement which comprises adding an additive consisting essentially of at least one isoalkane containing 6–10 carbon atoms per molecule to a liquid feed comprising at least one isopentane so as to increase the conversion of said at least one isopentane to isobutane and to product alkanes containing at least 6 carbon atoms per molecule;

wherein said catalyst consists essentially of liquid anhydrous hydrogen fluoride, alkenes are substantially absent from said liquid feed, and the weight ratio of said additive to said at least one isopentane contained in said liquid feed is about 0.02:1 to about 1:1.

2. A process in accordance with claim 1, wherein said at least one isoalkane contains 6–8 carbon atoms per molecule.

3. A process in accordance with claim 2, wherein said at least one isoalkane is selected from the group consisting of 2,3-dimethylbutane, 2,3-dimethylpentane and 2,2,4-trimethylpentane.

TABLE I

|  | Run 1 (Control) | Run 2 (Control) | Run 3 (Invention) | Run 4 (Invention) | Run 5 (Invention) | Run 6 (Invention) |
|---|---|---|---|---|---|---|
| Reaction Temperature °F. | 182 | 195 | 190 | 189 | 190 | 202 |
| Feed Composition (Weight-%) | | | | | | |
| Isobutane | 0.02 | 0.06 | 0.00 | 0.00 | 0.01 | — |
| Isopentane | 98.64 | 99.00 | 64.37 | 70.33 | 64.47 | ~94.8 |
| n-Pentane | 0.62 | 0.38 | 0.02 | 0.43 | 0.41 | — |
| n-Hexane | 0.72 | 0.00 | 0.49 | 0.53 | 0.47 | — |
| 2,3-dimethylbutane | — | — | 35.12 | — | — | — |
| 2,3-dimethylpentane | — | — | — | 28.53 | — | — |
| 2,2,4-trimethylpentane | — | — | — | — | 34.60 | — |
| $C_{12}$–$C_{16}$ Isoalkanes* | — | — | — | — | — | 5.14 |
| Product Composition (Weight-%) | | | | | | |
| Propane | 0.03 | 0.01 | 0.40 | 0.52 | 0.25 | 0.03 |
| Isobutane | 2.27 | 7.05 | 14.11 | 16.87 | 32.18 | 11.54 |
| n-Butane | 0.03 | 0.11 | 0.18 | 0.32 | 1.76 | 0.19 |
| Isopentane | 92.18 | 79.36 | 30.09 | 26.86 | 24.83 | 65.82 |
| n-Pentane | 0.83 | 0.95 | 1.03 | 1.23 | 1.61 | 0.62 |
| $C_6$ Hydrocarbons | 4.14 | 11.06 | 35.41[1] | 20.79 | 16.04 | 15.79 |
| $C_7$ Hydrocarbons | 0.08 | 0.74 | 10.57 | 19.77 | 8.80 | 1.89 |
| $C_8$ Hydrocarbons | 0.10 | 0.11 | 3.22 | 6.70 | 5.49 | 0.64 |
| $C_9$+ Hydrocarbons | 0.35 | 0.62 | 5.01 | 6.95 | 9.04 | 3.49 |
| Conversion of isopentane (%) | 7.8 | 19.8 | 53.3 | 61.8 | 61.5 | 29.9 |

*marketed as "Soltrol 220" by Phillips Chemical Company, Bartlesville, Oklahoma
[1]about 0.8 weight-% 2,2-dimethylbutane, about 7.3 weight-% 2,3-dimethylbutane, about 17.3 weight-% 2-methylpentane, about 9.0 weight-% 3-methylpentane and about 0.9 weight-% n-hexane.

Test data in Table I clearly show the surprising effect of the presence of higher isoalkanes on isopentane conversion. In the case of the addition of an isohexane (Run 3), the total amounts of isohexanes in the product was approximately the same as the amount of the isohexane additive in the feed. It is envisioned that the isohexanes can be recycled to the reactor (along with unconverted isopentane and HF), so that the enhanced conversion of isopentane to isobutane and $C_7$+ hydrocarbons is essentially the net result of this preferred embodiment of the present invention.

Reasonable variations, modifications and adaptations for various usages and conditions can be made within the scope of the disclosure and the appended claims, without departing from the scope of this invention.

4. A process in accordance with claim 1, wherein said weight ratio of said additive to said at least one isopentane contained in said liquid feed is about 0.05:1 to about 1:1.

5. A process in accordance with claim 4, wherein said weight ratio is about 0.1 to about 1:1.

6. A process in accordance with claim 1, wherein said liquid feed contains more than about 50 weight percent of said at least one isopentane.

7. A process in accordance with claim 6, wherein the volume ratio of said liquid anhydrous hydrogen fluoride to said liquid feed comprising more than about 50 weight percent of said at least one isopentane is in the range of about 0.1:1 to about 4:1.

8. A process in accordance with claim 7, wherein said volume ratio is in the range of about 1:1 to about 3:1.

9. A process in accordance with claim 7, being carried out at a temperature of about 100°–250° F. and a pressure of about 200–400 psig.

10. A process in accordance with claim 9, wherein said temperature is about 180°–210° F. and said additive consists essentially of at least an isoalkane containing 6–8 carbon atoms per molecule.

11. A process in accordance with claim 6, wherein said liquid feed contains about 60–99.99 weight percent of said at least one isopentane.

12. A process in accordance with claim 1, wherein formed alkanes are also recovered from the product of said process.

13. A process in accordance with claim 12, wherein hydrogen fluoride, at least one unconverted isopentane and unconverted additive are also recovered from said product.

14. In a process for disproportionating isopentanes in the presence of a catalyst so as to form alkanes containing fewer than five carbon atoms per molecule and alkanes containing more than five carbon atoms per molecule, the improvement which comprises adding an additive consisting essentially of at least one isoalkane containing 6–18 carbon atoms per molecule to a liquid feed comprising at least one isopentane so as to increase the conversion of said at least one isopentane to isobutane and to product alkanes containing at least 6 carbon atoms per molecule;

wherein said catalyst consists essentially of liquid anhydrous hydrogen fluoride, alkenes are substantially absent from said liquid feed, and the weight ratio of said additive to said at least one isopentane is about 0.02:1 to about 1:1.

15. A process in accordance with claim 14, wherein said at least one isoalkane contains 12–16 carbon atoms per molecule.

16. A process in accordance with claim 15, wherein the weight ratio of said additive to said at least one isopentane contained in said liquid feed is about 0.05:1 to about 1:1.

17. A process in accordance with claim 16, wherein said weight ratio is about 0.1:1 to about 1:1.

18. A process in accordance with claim 14, wherein said liquid feed contains more than about 50 weight percent of said at least one isopentane.

19. A process in accordance with claim 18, wherein the volume ratio of said liquid anhydrous hydrogen fluoride to said liquid feed comprising more than about 50 weight-% of said at least one isopentane is in the range of about 0.1:1 to about 4:1.

20. A process in accordance with claim 19, wherein said volume ratio is in the range of about 1:1 to about 3:1.

21. A process in accordance with claim 19, being carried out at a temperature of about 100°–250° F. and a pressure of about 200–400 psig.

22. A process in accordance with claim 21, wherein said temperature is about 180°–210° F., and said additive consists essentially of at least one isoalkane containing 12–16 carbon atoms per molecule.

23. A process in accordance with claim 18, wherein said liquid feed contains about 60–99.99 weight percent of said at least one isopentane.

24. A process in accordance with claim 14, wherein formed alkanes are recovered from the product of said process.

25. A process in accordance with claim 24, wherein hydrogen fluoride, at least one unconverted isopentane and unconverted additive are also recovered from said product.

* * * * *

UNITED STATES PATENT AND TRADEMARK OFFICE
CERTIFICATE OF CORRECTION

PATENT NO. : 5,489,727

DATED : Feb. 6, 1996

INVENTOR(S) : Bruce B. Randolph et al

It is certified that error appears in the above-identified patent and that said Letters Patent is hereby corrected as shown below:

Claim 12, column 5, line 12, delete ". also".

Signed and Sealed this

Twenty-first Day of May, 1996

*Attest:*

BRUCE LEHMAN

*Attesting Officer*     *Commissioner of Patents and Trademarks*